United States Patent
Pang et al.

(10) Patent No.: US 10,739,134 B2
(45) Date of Patent: Aug. 11, 2020

(54) METHOD AND SYSTEM FOR DETECTING FINGERPRINT SENSOR PROTECTION LAYER THICKNESS

(71) Applicant: SHENZHEN GOODIX TECHNOLOGY CO., LTD., Shenzhen, Guangdong (CN)

(72) Inventors: Shu Pang, Guangdong (CN); Xiaochun Cai, Guangdong (CN)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 521 days.

(21) Appl. No.: 15/676,205

(22) Filed: Aug. 14, 2017

(65) Prior Publication Data
US 2017/0343341 A1 Nov. 30, 2017

Related U.S. Application Data

(63) Continuation of application No. PCT/CN2016/091673, filed on Jul. 26, 2016.

(30) Foreign Application Priority Data

Dec. 18, 2015 (CN) .......................... 2015 1 0956858

(51) Int. Cl.
*G01B 21/08* (2006.01)
*G01B 7/06* (2006.01)
(Continued)

(52) U.S. Cl.
CPC .............. *G01B 21/08* (2013.01); *G01B 7/06* (2013.01); *G06K 9/0002* (2013.01); *G06K 9/00053* (2013.01); *A61B 5/117* (2013.01)

(58) Field of Classification Search
CPC ........ G01B 21/08; G01B 7/06; G06K 9/0002; G06K 9/00053
See application file for complete search history.

(56) References Cited

U.S. PATENT DOCUMENTS 6,693,441 B2 * 2/2004 Lane .................... G06K 9/0002
 324/662
9,811,711 B2 * 11/2017 Huang ...................... G02B 5/20

FOREIGN PATENT DOCUMENTS

| CN | 1278347 A | 12/2000 |
|---|---|---|
| CN | 1440060 A | 9/2003 |

(Continued)

OTHER PUBLICATIONS

State Intellectual Property Office of the P.R. China (ISR/CN), "International Search Report for PCT/CN2016/091673", China, dated Oct. 31, 2016.

*Primary Examiner* — Janet L Suglo
(74) *Attorney, Agent, or Firm* — Heslin Rothenberg Farley & Mesiti P.C.

(57) ABSTRACT

Embodiments of the present invention relate to the technical field of fingerprint sensor detection, and in particular, relate to a method and system for detecting a thickness of a protection layer of a fingerprint sensor. The method includes the following steps: step a: collecting fingerprint data via a fingerprint sensor, the fingerprint sensor comprising a plurality of chip sensing units, arranged in an array; step b: calculating a derivative of the fingerprint data, normalizing the derivative of the fingerprint data, and calculating an integration according to the normalized derivative of the fingerprint data; and step c: acquiring a thickness of a protection layer of the fingerprint sensor according to the integration result.

12 Claims, 3 Drawing Sheets

(51) Int. Cl.
*G06K 9/00* (2006.01)
*A61B 5/117* (2016.01)

(56) References Cited

FOREIGN PATENT DOCUMENTS

| | | |
|---|---|---|
| CN | 102564326 A | 7/2012 |
| CN | 103206914 A | 7/2013 |
| CN | 104102902 A | 10/2014 |
| JP | 2002224087 A | 8/2002 |
| WO | 2006118812 A2 | 11/2006 |
| WO | 2012062343 A1 | 5/2012 |

* cited by examiner

METHOD AND SYSTEM FOR DETECTING FINGERPRINT SENSOR PROTECTION LAYER THICKNESS

CROSS-REFERENCE TO RELATED APPLICATIONS

This application is a continuation of international application No. PCT/CN2016/091673, filed on Jul. 26, 2016, which claims priority to Chinese Patent Application No. 201510956858.X, filed before Chinese Patent Office on Dec. 18, 2015, both of which are incorporated herein by reference in their entities.

TECHNICAL FIELD

The present invention relates to the technical field of fingerprint sensor detection, and in particular, relates to a method and a system for detecting a thickness of a protection layer of a fingerprint sensor.

BACKGROUND

Fingerprints refer to textures formed by uneven skin surface of fingers. The fingerprint has unique and stable texture characteristics, and is generally used as a basis for identity recognition. A fingerprint sensor is a sensor for identity recognition by using the fingerprint.

FIG. 1 is a schematic structural diagram of a conventional fingerprint sensor. The fingerprint sensor includes a covering layer 11, an adhesive 12 and a fingerprint sensor chip 13. The covering layer 11 may be made from glass, sapphire, coating or the like, and is mainly intended to protect the fingerprint sensor chip 13. The adhesive 12 is adapted for fixing the covering layer 11 to the fingerprint sensor chip. The fingerprint sensor chip 13 includes a matrix formed of thousands of pixels 14 (chip sensing units). When a finger presses the fingerprint sensor, the pixel 14 senses a fingerprint texture depth of the finger 15 thereon, and a matrix formed of fingerprint text depth data output by all the pixels 14 constitutes fingerprint texture information of the finger 15.

The protection layer (including the covering layer 11 and the adhesive 12) of the fingerprint sensor is between the finger 15 and the fingerprint sensor chip 13. Therefore, the thickness of the protection layer may affect the signal-to-noise ratio of the fingerprint texture depth data collected by the fingerprint sensor, and accordingly directly affect the fingerprint texture depth data acquired by the fingerprint sensor. If the protection layer of the fingerprint sensor is too thick or too thin, performance of the product and user experience may all be directly impacted. Therefore, the thickness of the protection layer of the fingerprint needs to be strictly controlled.

Since a frame of the fingerprint sensor is generally wrapped by a protective or decorative material, the thickness of the protection layer may not be directly measured from a side of the fingerprint sensor. A conventional method for measuring the thickness of a protection layer is to directly cutting off the fingerprint sensor and then measuring the thickness of the protection layer by using a microscope. However, the method is defective in that the fingerprint sensor needs to be destroyed for the measurement; and therefore only sample detection may be carried out during mass production, measurement may not carried out for all the fingerprint sensors, and moreover, the measurement cost is high.

SUMMARY

The present invention provides a method and system for detecting a thickness of a protection layer of a fingerprint sensor, which are intended to solve the technical problems that in the convention method for detecting a thickness of a protection layer of a fingerprint sensor, sample detection may only be implemented, measurement may not carried out for all the fingerprint sensors, and the measurement cost is high.

To solve the above technical problem, one technical solution employed by embodiments of the present invention is a method for detecting a thickness of a protection layer of a fingerprint sensor. The method includes the following steps:

step a: collecting fingerprint data via a fingerprint sensor, the fingerprint sensor including a plurality of chip sensing units, being arranged in an array;

step b: calculating a derivative of the fingerprint data, normalizing the derivative of the fingerprint data, and calculating an integration of the fingerprint data according to the normalized derivative of the fingerprint data; and step c: acquiring a thickness of a protection layer of the fingerprint sensor according to the integration of the fingerprint sensor.

In this technical solution employed by embodiments of the present invention, step a further includes: pressing the fingerprint sensor by using a fingerprint simulating device; wherein the fingerprint simulating device is a prosthetic finger including an object that has electrical features or is approximate to a finger.

In this technical solution employed by embodiments of the present invention, in step b, the derivative of the fingerprint data is calculated by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2}$$

wherein $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column.

In this technical solution employed by embodiments of the present invention, in step b, the derivative of the fingerprint data is normalized by using the following formula:

$$Q_{i,j} = \frac{D_{i,j} - D_{min}}{D_{max} - D_{min}}$$

wherein $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the current frame of fingerprint data.

In this technical solution employed by embodiments of the present invention, in step b, the integration of the fingerprint sensor is calculated by using the following formula:

$$I = \Sigma_{i=0}^{row} \Sigma_{j=0}^{col} Q_{i,j}$$

wherein I denotes an integration result, row denotes a total number of rows of the chip sensing units, and col denotes a total number of columns of the chip sensing units.

In this technical solution employed by embodiments of the present invention, in step c, the thickness of the protection layer of the fingerprint sensor is calculated by using a linear fitting formula:

$$T = K \times I + B$$

wherein T denotes a calculated thickness of the protection layer, and K and B denote fitting parameters.

Another technical solution employed by embodiments of the present invention is a system for detecting a thickness of a protection layer of a fingerprint sensor. The system includes: a fingerprint collecting unit, a derivative calculating unit, a derivative normalizing unit, an integration calculating unit and a protection layer thickness calculating unit; wherein the fingerprint collecting unit, the derivative calculating unit, the derivative normalizing unit, the integration calculating unit and the protection layer thickness calculating unit are sequentially connected;

the fingerprint collecting unit is configured to collect fingerprint data and includes a plurality of chip sensing units, arranged in an array;

the derivative calculating unit is configured to calculate a derivative of the fingerprint data;

the derivative normalizing unit is configured to normalize the derivative of the fingerprint data;

the integration calculating unit is configured to calculate an integration according to the normalized derivative of the fingerprint data; and the protection layer thickness calculating unit is configured to calculate a thickness of the protection layer of the fingerprint sensor according to an integration result.

In this technical solution employed by embodiments of the present invention, the system further includes: a fingerprint simulating device, connected to the fingerprint collecting unit, the fingerprint simulating device is configured to simulate a finger to press the fingerprint sensor, and the fingerprint simulating device is a prosthetic finger including an object that has electrical features or is approximate to a finger.

In this technical solution employed by embodiments of the present invention, the derivative calculating unit calculates the derivative of the fingerprint data by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2}$$

wherein $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column; and the derivative normalizing unit normalizes the derivative of the fingerprint data by using the following formula:

$$Q_{i,j} = \frac{D_{i,j} - D_{min}}{D_{max} - D_{min}}$$

wherein $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the current frame of fingerprint data.

In this technical solution employed by embodiments of the present invention, the integration calculating unit calculates the integration of the fingerprint sensor by using the following formula:

$$I = \Sigma_{i=0}^{row} \Sigma_{j=0}^{col} Q_{i,j}$$

wherein I denotes an integration result, row denotes the total number of rows of the chip sensing units, and col denotes the total number of columns of the chip sensing units;

the protection layer thickness calculating unit calculates the thickness of the protection layer of the sensor by using a linear fitting formula:

$$T = K \times I + B$$

wherein T denotes a calculated thickness of the protection layer, and K and B denote fitting parameters.

As compared with the prior art, the present invention has the following beneficial effects: In the method and system for detecting a thickness of a protection layer of a fingerprint sensor according to the embodiments of the present invention, the thickness of the protection layer of the fingerprint sensor is calculated according to the fingerprint data acquired by the fingerprint sensor, and thus the thickness of the protection layer of the fingerprint sensor may be measured without causing damages to the fingerprint sensor; during mass production, measurement may be carried out for each sensor, and thus product quality may be better controlled; and the measurement cost is low.

DETAILED DESCRIPTION

For better understanding of the present invention, the present invention is thoroughly described with reference to relevant accompanying drawings. The accompanying drawings show preferential embodiments of the present invention. However, the present invention may be implemented in a plurality of forms or ways, and is not limited to the embodiments described herein. On the contrary, the embodiments described herein are intended to make the disclosure of the present invention more clearly and thoroughly understood.

Unless otherwise defined, all the technical and scientific terms used in this specification convey the same meanings as the meanings commonly understood by a person skilled in the art. Additionally, the terms used in the specification the present invention are merely for describing the objective of the specific embodiments, and are not intended to limit the present invention.

Figure 1:
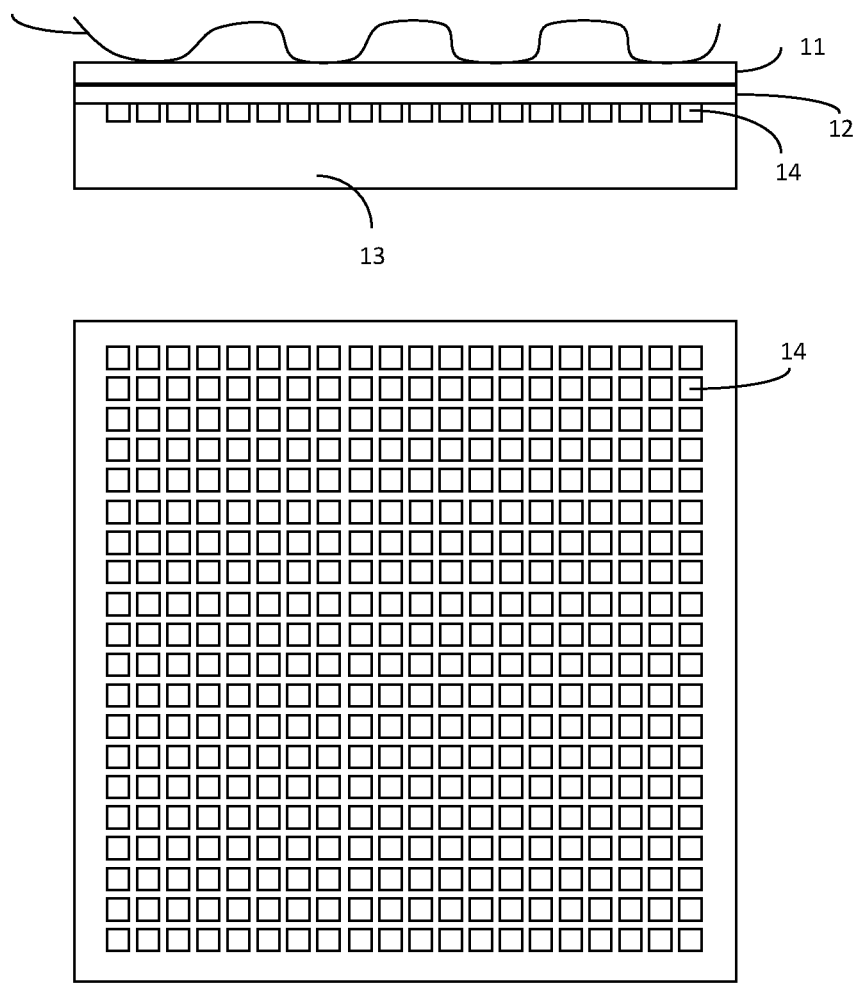
FIG. 1 is a schematic structural diagram of a conventional fingerprint sensor.
Figure 2:
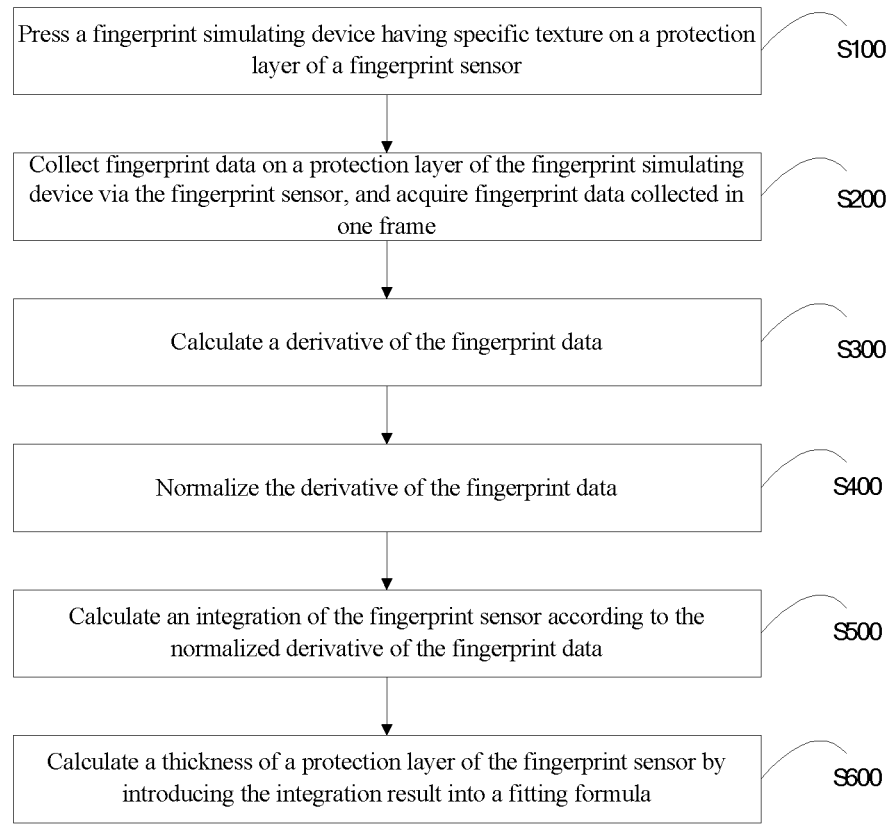
FIG. 2 is a flowchart of a method for detecting a thickness of a protection layer of a fingerprint sensor according to an embodiment of the present invention.

FIG. 2 is a flowchart of a method for detecting a thickness of a protection layer of a fingerprint sensor according to an embodiment of the present invention. The method for detecting a thickness of a protection layer of a fingerprint sensor includes the following steps:

Step S100: A fingerprint simulating device having specific texture is pressed on a protection layer of a fingerprint sensor.

Figure 3:
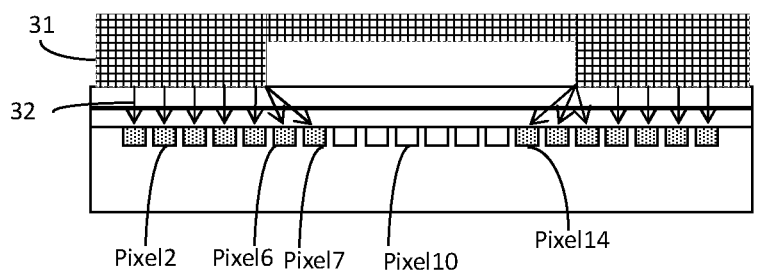
FIG. 3 is a diagram illustrating signal scattering of a fingerprint sensor.
Figure 4:
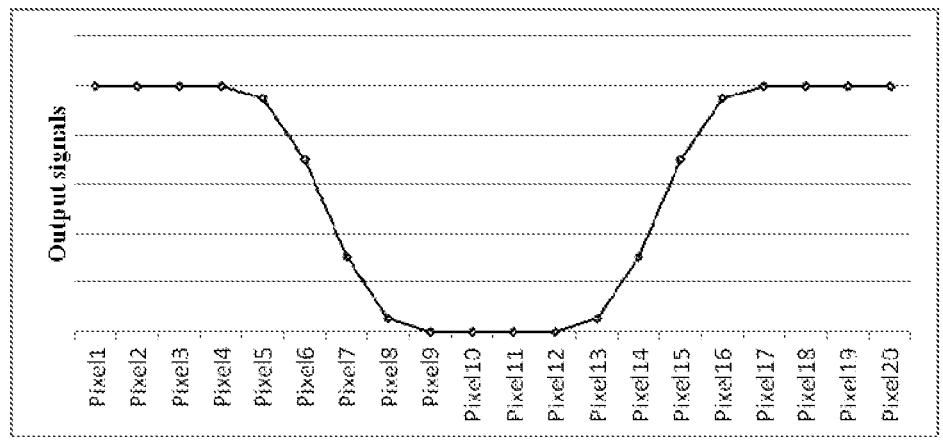
FIG. 4 is a schematic diagram illustrating strength of an output signal of a chip sensing unit.

In step S100, referring to FIG. 3, a signal scattering diagram of the fingerprint sensor is illustrated. The fingerprint sensor includes a plurality of chip sensing units (pixels), which are arranged in an array. Fingerprint texture depth data output by the chip sensing unit reflects fingerprint texture information. When a fingerprint simulating device 31 presses the fingerprint sensor, a press signal may be generated in a contact position between the fingerprint simulating device 31 and the fingerprint sensor, and then the press signal is received by the chip sensing unit arranged below the contact position. Since a covering layer and an adhesive are sandwiched between the fingerprint simulating device and the chip sensing unit, the press signal is scattered to the chip sensing unit in the manner as illustrated by an arrow 32 in FIG. 3. Although right top portions of some chip sensing units are not pressed by the fingerprint simulating device, these chip sensing units may still receive the press signal of the fingerprint simulating device scattered from oblique top portions thereof. Therefore, these chip sensing units still output signals which are less than signals output by the chip sensing units that are directly pressed at the right top portions thereof. As illustrated in FIG. 3, Pixel 2 is a chip sensing unit that is directly pressed, and Pixel 6, Pixel 7 and Pixel 14 are chip sensing units that are not pressed by the fingerprint simulating device but may still receive the scattered signals from the oblique top portions. Such a chip sensing unit as Pixel 10 that is neither directly pressed nor receives any scattered signal output no signal (which outputs noise only). Specifically, FIG. 4 is a schematic diagram illustrating strengths of output signals of all chip sensing units.

Figure 5:
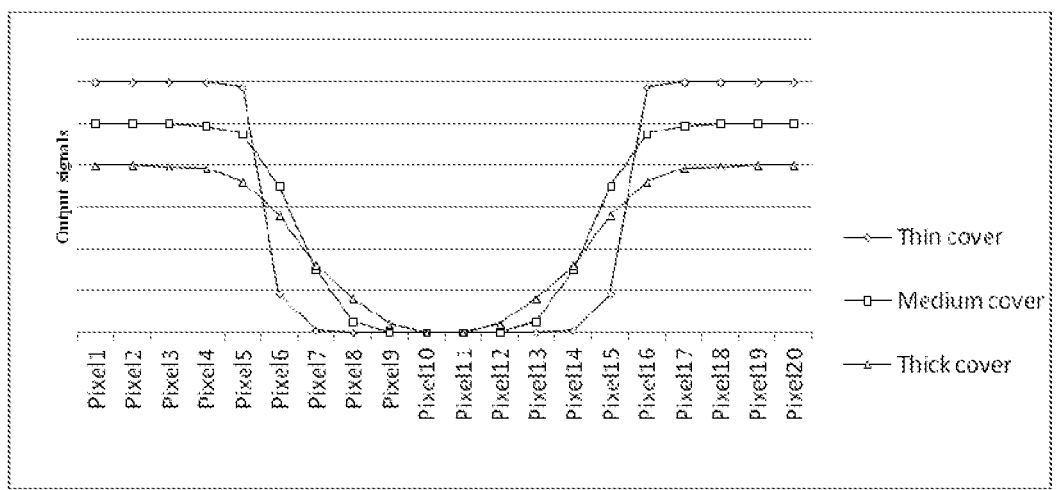
FIG. 5 is a comparison diagram of strengths of output signals of chip sensing units having protection layers with different thicknesses.

Experiments find that the range and strength of scattering of the press signal of the fingerprint simulating device is relevant to the thickness of the protection layer. FIG. 5 is a comparison diagram of strengths of output signals of chip sensing units having protection layers with different thicknesses. A greater thickness of the protection layer indicates a larger scattering range of the press signal and a smaller curve slope of the signal output by the chip sensing unit. The method for detecting a thickness of a protection layer of a fingerprint sensor according to the present invention implements thickness detection based on the above scattering feature of the press signal. In the embodiment of the present invention, the fingerprint simulating device may be a prosthetic finger including an object that has electrical features or is approximate to a finger, for example, a metal block, an electrically conductive rubber and the like. No special requirement is imposed on the specific texture of the prosthetic finger. However, textures of prosthetic fingers calculated by using the same calculation formula need to be identical.

Step S200: Fingerprint data on a protection layer of the fingerprint simulating device is collected via the fingerprint sensor, and a frame of fingerprint data is acquired.

Step S300: A derivative of the fingerprint data is calculated, wherein the derivative of the fingerprint data is calculated by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2} \quad (1)$$

In formula (1), $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column.

Step S400: The derivative of the fingerprint data is normalized, wherein the derivative of the fingerprint data is normalized by using the following formula:

$$Q_{i,j} = \frac{D_{i,j} - D_{min}}{D_{max} - D_{min}} \quad (2)$$

In formula (2), $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the current frame of fingerprint data.

Step S500: An integration of the fingerprint sensor is calculated according to the normalized derivative of the fingerprint data, wherein the integration of the fingerprint sensor is calculated by using the following formula:

$$I = \Sigma_{i=0}^{row} \Sigma_{j=0}^{col} Q_{i,j} \quad (3)$$

In formula (3), I denotes an integration result, row denotes a total number of rows of pixels, and col denotes a total number of columns of the pixels.

Step S600: A thickness of a protection layer of the fingerprint sensor is calculated by introducing the integration result into a fitting formula.

In step S600, different fitting formulas may be used according to the specific relationships. In the embodiment of the present invention, the thickness of the protection layer is calculated a linear fitting formula:

$$T = K \times I + B \quad (4)$$

In formula (4), T denotes a calculated thickness of the protection layer, and K and B denote fitting parameters. The fitting parameters are calculated by using such methods as the least square method and the like. Firstly, integration results I of a plurality of fingerprint sensors need to be collected and calculated through steps 200 to 500, then the thicknesses of the protection layers of these fingerprint sensors are calculated, and finally the fitting parameters K and B are calculated according to the integration results I and the thicknesses T of the protection layers.

Figure 6:
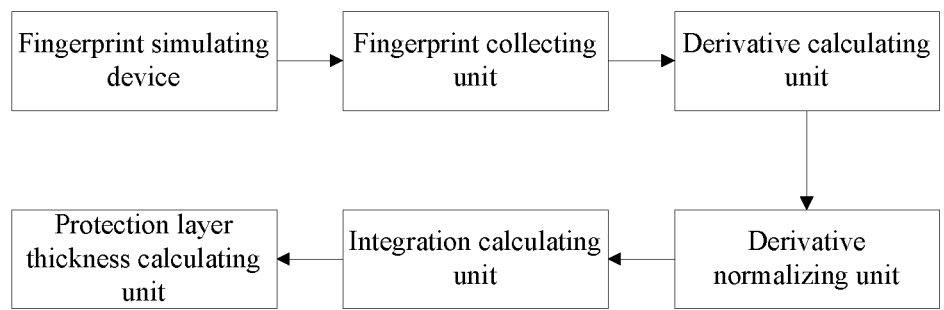
FIG. 6 is a schematic structural diagram of a system for detecting a thickness of a protection layer of a fingerprint sensor according to an embodiment of the present invention.

FIG. 6 is a schematic structural diagram of a system for detecting a thickness of a protection layer of a fingerprint sensor according to an embodiment of the present invention. The system for detecting a thickness of a protection layer of a fingerprint sensor includes: a fingerprint simulating device, a fingerprint collecting unit, a derivative calculating unit, a derivative normalizing unit, an integration calculating unit and a protection layer thickness calculating unit; wherein the fingerprint simulating device, the fingerprint collecting unit, the derivative calculating unit, the derivative normalizing unit, the integration calculating unit and the protection layer thickness calculating unit are sequentially connected.

The fingerprint simulating device is configured to simulate a finger to press a protection layer of a fingerprint sensor.

In the embodiment of the present invention, the fingerprint simulating device may be a prosthetic finger including an object that has electrical features or is approximate to a finger, for example, a metal block, an electrically conductive rubber and the like. No special requirement is imposed on the specific texture of the prosthetic finger. However, textures of prosthetic fingers calculated by using the same calculation formula need to be identical.

The fingerprint collecting unit is configured to collect fingerprint data on the protection layer of the fingerprint simulating device, to acquire a frame of fingerprint data; wherein the fingerprint collecting unit is an array of chip sensing units.

The derivative calculating unit is configured to calculate a derivative of the fingerprint data, wherein the derivative of the fingerprint data is calculated by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2} \quad (1)$$

In formula (1), $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column.

The derivative normalizing unit is configured to normalize the derivative of the fingerprint data, wherein the derivative of the fingerprint data is normalized by using the following formula:

$$Q_{i,j} = \frac{D_{i,j} - D_{min}}{D_{max} - D_{min}} \quad (2)$$

In formula (2), $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the current frame of fingerprint data.

The integration calculating unit is configured to calculate an integration of the fingerprint sensor according to the normalized derivative of the fingerprint data, wherein the integration of the fingerprint sensor is calculated by using the following formula:

$$I = \Sigma_{i=0}^{row} \Sigma_{j=0}^{col} Q_{i,j} \quad (3)$$

In formula (3), I denotes an integration result, row denotes the total number of rows of pixels, and col denotes the total number of columns of the pixels.

The protection layer thickness calculating unit is configured to calculate a thickness of a protection layer of the fingerprint sensor by introducing the integration result into a fitting formula; wherein different fitting formulas may be used according to the specific relationships. In the embodiment of the present invention, the thickness of the protection layer is calculated a linear fitting formula:

$$T = K \times I + B \quad (4)$$

In formula (4), T denotes a calculated thickness of the protection layer, and K and B denote fitting parameters. The fitting parameters are calculated by using such methods as the least square method and the like. Firstly, integration results I of a plurality of fingerprint sensors need to be collected and calculated by sequentially using the fingerprint collecting unit, the derivative calculating unit, the derivative normalizing unit and the integration calculating unit, then the thicknesses of the protection layers of these fingerprint sensors are calculated, and finally the fitting parameters K and B are calculated according to the integration results I and the thicknesses T of the protection layers.

In the method and system for detecting a thickness of a protection layer of a fingerprint sensor according to the embodiments of the present invention, the thickness of the protection layer of the fingerprint sensor is calculated according to the fingerprint data collected by the fingerprint sensor, and thus the thickness of the protection layer of the fingerprint sensor may be measured without damaging the fingerprint sensor. Moreover, measurement may be carried out for each sensor during mass production, and thus product quality may be better controlled and the measurement cost is low.

Described above are preferred embodiments of the present invention. However, implementation of the present invention is not limited to the above embodiments. Any variations, polishments, substitutions, combinations, or simplifications, or the like equivalent replacements made to the present invention without departing from the spiritual essence and principle of the present invention shall all be covered within the protection scope of the present invention.

What is claimed is:

1. A method for detecting a thickness of a protection layer of a fingerprint sensor, the method comprising:
    step a: collecting fingerprint data via a fingerprint sensor, the fingerprint sensor comprising a plurality of chip sensing units arranged in an array;
    step b: calculating a derivative of the fingerprint data, normalizing the derivative of the fingerprint data, and calculating an integration according to the normalized derivative of the fingerprint data; and
    step c: acquiring a thickness of a protection layer of the fingerprint sensor according to the integration result.

2. The method for detecting a thickness of a protection layer of a fingerprint sensor according to claim 1, wherein step a further comprises:
    pressing the fingerprint sensor by using a fingerprint simulating device, wherein the fingerprint simulating device is a prosthetic finger comprising an object that has electrical features or is approximate to a finger.

3. The method for detecting a thickness of a protection layer of a fingerprint sensor according to claim 1, wherein in step b, the derivative of the fingerprint data is calculated by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2}$$

wherein $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column.

4. The method for detecting a thickness of a protection layer of a fingerprint sensor according to claim 3, wherein in step b, the derivative of the fingerprint data is normalized by using the following formula:

$$Q_{i,j} = \frac{D_{i,j} - D_{min}}{D_{max} - D_{min}}$$

wherein $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the current frame of fingerprint data.

5. The method for detecting a thickness of a protection layer of a fingerprint sensor according to claim 4, wherein in step b, the integration is calculated by using the following formula:

$$I = \Sigma_{i=0}^{row} \Sigma_{j=0}^{col} Q_{i,j}$$

wherein I denotes an integration result, row denotes a total number of rows of the chip sensing units, and col denotes a total number of columns of the chip sensing units.

6. The method for detecting a thickness of a protection layer of a fingerprint sensor according to claim 4, wherein in step c, the thickness of the protection layer of the fingerprint sensor is calculated by using a linear fitting formula:

$$T = K \times I + B$$

wherein T denotes a calculated thickness of the protection layer, and K and B denote fitting parameters.

7. A system for detecting a thickness of a protection layer of a fingerprint sensor, comprising: a fingerprint collecting unit, a derivative calculating unit, a derivative normalizing unit, an integration calculating unit and a protection layer thickness calculating unit; wherein the fingerprint collecting unit, the derivative calculating unit, the derivative normalizing unit, the integration calculating unit and the protection layer thickness calculating unit are sequentially connected;
the fingerprint collecting unit is configured to collect fingerprint data and comprises a plurality of chip sensing units arranged in an array;
the derivative calculating unit is configured to calculate a derivative of the fingerprint data;
the derivative normalizing unit is configured to normalize the derivative of the fingerprint data;
the integration calculating unit is configured to calculate an integration according to the normalized derivative of the fingerprint data; and
the protection layer thickness calculating unit is configured to calculate a thickness of the protection layer of the fingerprint sensor according to an integration result.

8. The system for detecting a thickness of a protection layer of a fingerprint sensor according to claim 7, further comprising a fingerprint simulating device connected to the fingerprint collecting unit, the fingerprint simulating device is configured to simulate a finger to press the fingerprint sensor, and the fingerprint simulating device is a prosthetic finger comprising an object that has electrical features or is approximate to a finger.

9. The system for detecting a thickness of a protection layer of a fingerprint sensor according to claim 7, wherein the derivative calculating unit calculates the derivative of the fingerprint data by using the following formula:

$$D_{i,j} = \sqrt{\left(\frac{R_{i+1,j} - R_{i-1,j}}{2}\right)^2 + \left(\frac{R_{i,j+1} - R_{i,j-1}}{2}\right)^2}$$

wherein $D_{i,j}$ denotes a derivative of a chip sensing unit in the $i^{th}$ row and $j^{th}$ column, and $R_{i,j}$ denotes fingerprint data of the chip sensing unit in the $i^{th}$ row and $j^{th}$ column.

10. The system for detecting a thickness of a protection layer of a fingerprint sensor according to claim 9, wherein the derivative normalizing unit normalizes the derivative of the fingerprint data by using the following formula:

$$Q_{i,j} = \frac{D_{i,j} - D_{min}}{D_{max} - D_{min}}$$

wherein $Q_{i,j}$ denotes a normalization result of the derivative of the chip sensing unit in the $i^{th}$ row and $j^{th}$ column, $D_{max}$ denotes a maximum derivative value of a current frame of fingerprint data, and $D_{min}$ denotes a minimum derivative value of the derivative of the current frame of fingerprint data.

11. The system for detecting a thickness of a protection layer of a fingerprint sensor according to claim 10, wherein the integration calculating unit calculates the integration by using the following formula:

$$I = \Sigma_{i=0}^{row} \Sigma_{j=0}^{col} Q_{i,j}$$

wherein I denotes an integration result, row denotes a total number of rows of the chip sensing units, and col denotes a total number of columns of the chip sensing units.

12. The system for detecting a thickness of a protection layer of a fingerprint sensor according to claim 9, wherein the protection layer thickness calculating unit calculates the thickness of the protection layer of the sensor by using a linear fitting formula:

$$T = K \times I + B$$

wherein T denotes a calculated thickness of the protection layer, and K and B denote fitting parameters.

* * * * *